US011166624B2

(12) United States Patent
Ubbesen et al.

(10) Patent No.: US 11,166,624 B2
(45) Date of Patent: Nov. 9, 2021

(54) MEDICAL VISUALIZATION SYSTEM

(71) Applicant: AMBU A/S, Ballerup (DK)

(72) Inventors: Line Sandahl Ubbesen, Holte (DK); Brian Nielsen, Næstved (DK); Henrik Frengler, Værløse (DK); Christina Hahnemann, Charlottenlund (DK)

(73) Assignee: AMBU A/S, Ballerup (DK)

( * ) Notice: Subject to any disclaimer, the term of this patent is extended or adjusted under 35 U.S.C. 154(b) by 0 days.

(21) Appl. No.: 16/919,476

(22) Filed: Jul. 2, 2020

(65) Prior Publication Data

US 2021/0259522 A1 Aug. 26, 2021

(30) Foreign Application Priority Data

Feb. 21, 2020 (DK) .......................... PA 2020 70115
May 4, 2020 (DK) .......................... PA 2020 70283

(51) Int. Cl.
*A61B 1/00* (2006.01)
*A61B 1/307* (2006.01)
(Continued)

(52) U.S. Cl.
CPC ...... *A61B 1/00059* (2013.01); *A61B 1/00045* (2013.01); *A61B 1/00121* (2013.01);
(Continued)

(58) Field of Classification Search
CPC ............ A61B 1/00045; A61B 1/00059; A61B 1/00121; A61B 1/00144; A61B 1/04; A61B 1/233; A61B 90/92; A61B 2562/226

See application file for complete search history.

(56) References Cited

U.S. PATENT DOCUMENTS 5,836,869 A * 11/1998 Kudo ..................... A61B 90/92
600/173
6,059,719 A 5/2000 Yamamoto et al.
(Continued)

FOREIGN PATENT DOCUMENTS

| CN | 203861339 U | 10/2014 |
|---|---|---|
| DE | 202006008061 U1 | 8/2006 |
| EP | 3200109 A1 | 8/2017 |

OTHER PUBLICATIONS

International Search Report and Written Opinion issued in PCT/EP2021/053965, dated Apr. 7, 2021, 9 pages.
(Continued)

*Primary Examiner* — Aaron B Fairchild
(74) *Attorney, Agent, or Firm* — Faegre Drinker Biddle & Reath LLP (57) ABSTRACT

A medical visualisation system including a first medical visualisation device having a first device colour identifier, a second medical visualisation device having a second device colour identifier, a third medical visualisation device having a third device colour identifier, and a monitor device, the first device colour identifier being a first colour, the second device colour identifier being a second colour, and the third device colour identifier being a third colour. The first colour has a first hue angle, the second colour has a second hue angle, and the third colour has a third hue angle, wherein the first hue angle and the second hue angle differ by more than 40 degrees, the second hue angle and the third hue angle differ by more than 40 degrees, and the third hue angle and the first hue angle differ by more than 40 degrees.

21 Claims, 2 Drawing Sheets

(51) Int. Cl.
  *A61B 1/267*  (2006.01)
  *A61B 1/31*   (2006.01)
  *A61B 1/04*   (2006.01)
  *A61B 90/92*  (2016.01)
  *A61B 1/233*  (2006.01)
  *A61B 1/273*  (2006.01)

(52) U.S. Cl.
  CPC ............ *A61B 1/00144* (2013.01); *A61B 1/04* (2013.01); *A61B 1/233* (2013.01); *A61B 1/2676* (2013.01); *A61B 1/2736* (2013.01); *A61B 1/307* (2013.01); *A61B 1/31* (2013.01); *A61B 90/92* (2016.02); *A61B 2562/226* (2013.01)

(56) References Cited

U.S. PATENT DOCUMENTS

| | | | |
|---|---|---|---|
| 2002/0026199 A1* | 2/2002 | Fortier | A61B 17/00234 606/108 |
| 2015/0065807 A1 | 3/2015 | Greenberg et al. | |
| 2015/0092032 A1 | 4/2015 | Kuramoto | |

OTHER PUBLICATIONS

Search Report issued by the Danish Patent and Trademark Office, dated Jul. 27, 2020, for Application No. PA202070283; 9 pages.

\* cited by examiner

MEDICAL VISUALIZATION SYSTEM

CROSS-REFERENCE TO RELATED APPLICATIONS

This application claims priority from Denmark Patent Application No. PA 2020 70115, filed Feb. 21, 2020, and Denmark Patent Application No. PA 2020 70283, filed May 4, 2020, both applications incorporated herein by reference in their entirety.

TECHNICAL FIELD

The present disclosure relates to a medical visualisation system, such as a medical visualisation system comprising a plurality of medical visualisation devices, e.g. endoscopes, and a monitor device.

BACKGROUND

Medical visualisation devices, such as endoscopes may, although conceptually being alike, be used for very different medical procedures. Although conceptually being alike, the medical visualisation devices may still comprise important differences. Therefore, it is not unimportant what type of medical visualisation device is used in a given procedure.

For example, an endoscope may conceptually comprise a handle and an insertion tube extending from the handle to a distal tube end. The endoscope may be configured to generate a view from the distal tube end of the insertion tube. Furthermore, the handle may comprise control mechanisms to bend the distal tube end in various directions. However, endoscopes for different procedures may vary, e.g., by their control functionality, the diameter of the insertion tube, the length of the insertion tube, etc.

Although differences between endoscope types may be notably, it may be preferred if the intended use of endoscopes or other medical visualisation devices can be quickly identified.

SUMMARY

It is an object of the present disclosure to provide a medical visualisation system, which facilitates easy identification of device types, and their compatibility.

Thus, the present disclosure relates to a medical visualisation system comprising a plurality of medical visualisation devices, e.g. a first medical visualisation device, a second medical visualisation device, a third medical visualisation device. The medical visualisation system further comprises a monitor device.

The first medical visualisation device comprises a first image sensor and a first connector. The second medical visualisation device comprises a second image sensor and a second connector. The third medical visualisation device comprises a third image sensor and a third connector.

The monitor device comprises one or more connector ports. Each of the one or more connector ports is adapted to receive one or more of the first connector, the second connector and the third connector.

The first medical visualisation device may be a first device type configured for a first clinical purpose. The second medical visualisation device is a second device type configured for a second clinical purpose. The third medical visualisation device is a third device type configured for a third clinical purpose.

The first medical visualisation device comprises a first device colour identifier. The second medical visualisation device comprises a second device colour identifier. The third medical visualisation device comprises a third device colour identifier. The first device colour identifier is a first colour. The second device colour identifier is a second colour. The third device colour identifier is a third colour.

The first colour has a first hue angle. The second colour has a second hue angle. The third colour has a third hue angle. The first hue angle and the second hue angle differ by more than 40 degrees. The second hue angle and the third hue angle differ by more than 40 degrees. The third hue angle and the first hue angle differ by more than 40 degrees.

It is an advantage of the disclosure that easy identification of the device type is provided, which provides for faster retrieval of the correct device, and reduces the likelihood of unpacking a wrong device for a given clinical procedure. Distributing colours to the identifiers by specifying minimum differences between hue angles of different colour identifiers facilitates more easily distinguishable identifiers.

BRIEF DESCRIPTION OF THE FIGURES

Embodiments of the disclosure will be described in more detail in the following with regard to the accompanying figures. The figures show one way of implementing the present disclosure and are not to be construed as being limiting to other possible embodiments falling within the scope of the attached claim set.

DETAILED DESCRIPTION

Colours may be defined in many ways. For example, a colour may be defined by its relative amount of red, green and blue light, the "RGB" colour space, typically used in computer graphics. Alternatively, a colour may be defined by its relative amount of cyan, magenta, yellow and key dies, the CMYK colour space, typically used in printing. Other well-established colour systems are the colour spaces defined by the International Commission on Illumination (CIE), which, among others include CIEL*a*b* and CIELCh. Throughout the present disclosure, unless specified otherwise, colour parameters are given with reference to the CIELCh colour space, where lightness is in the range 0-100, chroma is in the range 0-100, and hue is in the range 0-360.

Some colour spaces, such as the HSL and CIELCh— colour spaces, are defined in terms of lightness, hue, and chroma/saturation. HSL is generally an alternative representation of the RGB colour space, while CIELCh is generally an alternative representation of the CIEL*a*b* colour space.

Lightness of a colour describes overall intensity of how light or dark a colour is. Lightness may be in the range of 0-100 (in other implementations the range may be 0 to 1). For the CIELCh and HSL colour spaces a Lightness of 0 is black, i.e. no light, while a Lightness of 100 is white, i.e. maximum light.

Hue is the term for the pure spectrum colours commonly referred to by the "colour names"—red, orange, yellow, blue, green, violet, etc.—which appear in the hue circle or rainbow. Hue may be represented quantitatively by a single number, e.g. corresponding to an angular position, e.g. in the range of 0-360 degrees, around a central or neutral point or axis on a colour space coordinate diagram (such as a chromaticity diagram) or colour wheel. For example, a Hue of 0 degrees may be a red colour, while a Hue of 180 degrees in the HSL colour space is a turquoise colour, a Hue of 180 degrees in the CIELCh colour space is a green colour.

Chroma or Saturation may be defined as the strength or dominance of the hue. On the outer edge of the hue wheel are the intensely saturated hues, towards the centre of the colour wheel, no hue dominates, and they become less and less saturated. Chroma or Saturation may be in the range of 0-100 (in other implementations the range may be 0 to 1). For a fully saturated colour, e.g. a pure colour, Chroma or Saturation may be 100. For a grey scale colour, e.g. no "colour", Chroma or Saturation may be 0.

As the hue angles designate descriptive colours, Hue angles may be used to designate colours allowing easy differentiation. Bigger angular hue differences between two colours makes the colours more descriptively different. Hence, it may be easier to orally refer to two different colours if they are spaced by a higher hue angle, since they may be described by their common names, red, orange, yellow, blue green, violet etc.

The first medical visualisation device is a first device type configured for a first clinical purpose. The first clinical purpose may be urology. For example, the first device type may be a urology endoscope, such as a cystoscope or a ureteroscope. The second medical visualisation device is a second device type device configured for a second clinical purpose. The second clinical purpose may be gastroenterology. For example, the second device type may be a gastrointestinal endoscope, such as a gastroscope, a duodenoscope or a colonoscope. The third medical visualisation device is a third device type configured for a third clinical purpose. The third clinical purpose may be pulmonology. For example, the third device type may be a pulmonology endoscope, such as a bronchoscope.

The medical visualisation system may comprise a fourth medical visualisation device comprising a fourth image sensor and a fourth connector. The fourth medical visualisation device may be a fourth device type, e.g. configured for a fourth clinical purpose. The fourth clinical purpose may be rhinoscopy. For example, the fourth device type may be a rhino-laryngoscope.

As seen from the examples, the second clinical purpose may be different from the first clinical purpose, the third clinical purpose may be different from the first clinical purpose and/or the second clinical purpose, and/or the fourth clinical purpose may be different from the first clinical purpose, the second clinical purpose and/or the third clinical purpose. The second device type may be different from the first device type, the third device type may be different from the first device type and/or the second device type, and/or the fourth device type may be different from the first device type, the second device type and/or the third device type.

The fourth medical visualisation device may comprise a fourth device colour identifier. The fourth device colour identifier may be a fourth colour. The fourth colour may have a fourth hue angle. The fourth hue angle may differ by more than 40 degrees from the first hue angle, the second hue angle, and/or the third hue angle.

The first hue angle and the second hue angle may differ by more than 80 degrees, e.g. by more than 140 degrees.

The first hue angle may be between 90-120 degrees. The second hue angle may be between 250-280 degrees. The third hue angle may be between 5-35 degrees. The fourth hue angle may be between 310-340 degrees.

The first colour may have a first chroma value. The first chroma value may be more than 10, such as more than 20, such as more than 35, such as more than 50, such as more than 60, such as more than 70. The second colour may have a second chroma value. The second chroma value may be more than 10, such as more than 20, such as more than 35. The third colour may have a third chroma value. The third chroma value may be more than 10, such as more than 20, such as more than 35, such as more than 50, such as more than 55. The fourth colour may have a fourth chroma value. The fourth chroma value may be more than 10, such as more than 20, such as more than 35, such as more than 50, such as more than 60.

The first colour may have a first lightness value. The first lightness value may be more than 5, such as more than 10, such as more than 20, such as more than 30, such as more than 50, such as more than 65. The second colour may have a second lightness value. The second lightness value may be more than 5, such as more than 10, such as more than 20, such as more than 25. The third colour may have a third lightness value. The third lightness value may be more than 5, such as more than 10, such as more than 20, such as more than 30. The fourth colour may have a fourth lightness value. The fourth lightness value may be more than 5, such as more than 10, such as more than 20, such as more than 30, such as more than 35.

The first colour may be Pantone 390, e.g. having a lightness value of approximately 74, a chroma value of approximately 77 and a hue angle of approximately 105 in the CIELCh colour space. The second colour may be Pantone 301, e.g. having a lightness value of approximately 31, a chroma value of approximately 39 and a hue angle of approximately 277 in the CIELCh colour space. The third colour may be Pantone 1945, e.g. having a lightness value of approximately 35, a chroma value of approximately 61 and a hue angle of approximately 15 in the CIELCh colour space. The fourth colour may be Pantone 2593, e.g. having a lightness value of approximately 37, a chroma value of approximately 66 and a hue angle of approximately 321 in the CIELCh colour space.

The first medical visualisation device, the second medical visualisation device, the third medical visualisation device and/or the fourth medical visualisation device each may comprise a handle and an insertion tube extending from the handle to a distal tube end. The handle, i.e. the handle of any of the first, second, third and/or fourth medical visualisation devices, may comprise one or more shell parts, e.g. a first shell part and/or a second shell part. The first shell part and the second shell part may be connectable or be connected to each other, e.g. by snap locking elements, ultrasonic welding and/or by glue. The handle may comprise one or more other parts, such as a control knob, a grip surface, a transition portion etc., which may be attached to the shell part(s) and/or may be maintained by the shell part(s). For example, the control knob may extend from the handle and be connected to a control mechanism supported by the first shell part and/or the second shell part. The grip surface may be provided to increase friction of the handle to facilitate a firm grip on the handle. The grip surface may be glued or ultrasonic welded to the surface of the shell part(s). A transition portion may be provided at the interface between the handle and the insertion tube. For example, the transition portion may enclose a proximal portion of the insertion tube. The transition portion may seal the interface between the handle and the insertion tube. For example, the transition portion may comprise or form a sealing member, such as a flexible part, e.g. configured to provide a tight seal around the proximal portion of the insertion tube.

The first device colour identifier may comprise one or more coloured portions of the handle and/or of the insertion tube of the first medical visualisation device. For example, the first device colour identifier may include colouring of a control knob of the first medical visualisation device and/or of an area of the handle near the insertion tube of the first medical visualisation device, such as the transition portion as described above. The majority, such as the remainder, of the handle, such as the shell part(s) of the handle, and/or the insertion tube of the first medical visualisation device may be a white, light greyish, dark greyish or black colour.

The second device colour identifier may comprise one or more coloured portions of the handle and/or of the insertion tube of the second medical visualisation device. For example, the second device colour identifier may include colouring of a control knob of the second medical visualisation device and/or of an area of the handle near the insertion tube of the second medical visualisation device, such as the transition portion as described above. The majority, such as the remainder, of the handle, such as the shell part(s) of the handle, and/or the insertion tube of the second medical visualisation device may be a white, light greyish, dark greyish or black colour.

The third device colour identifier may comprise one or more coloured portions of the handle and/or of the insertion tube of the third medical visualisation device. For example, the third device colour identifier may include colouring of a control knob of the third medical visualisation device and/or of an area of the handle near the insertion tube of the third medical visualisation device, such as the transition portion as described above. The majority, such as the remainder, of the handle, such as the shell part(s) of the handle, and/or the insertion tube of the third medical visualisation device may be a white, light greyish, dark greyish or black colour.

The fourth device colour identifier may comprise one or more coloured portions of the handle and/or of the insertion tube of the fourth medical visualisation device. For example, the fourth device colour identifier may include colouring of a control knob of the fourth medical visualisation device and/or of an area of the handle near the insertion tube of the fourth medical visualisation device, such as the transition portion as described above. The majority, such as the remainder, of the handle, such as the shell part(s) of the handle, and/or the insertion tube of the fourth medical visualisation device may be a white, light greyish, dark greyish or black colour.

Each of the medical visualisation device(s) may be individually packaged in a packaging, such as a sealed packaging, e.g. to maintain sterility of the device. The first medical visualisation device may be packaged in a first packaging. The second medical visualisation device may be packaged in a second packaging. The third medical visualisation device may be packaged in a third packaging. The fourth medical visualisation device may be packaged in a fourth packaging. The medical visualisation device(s) may be provided in a container comprising a plurality of medical visualisation devices. For example, the first medical visualisation device may be provided in a first container of a plurality of first medical visualisation devices. The second medical visualisation device may be provided in a second container of a plurality of second medical visualisation devices. The third medical visualisation device may be provided in a third container of a plurality of third medical visualisation devices. The fourth medical visualisation device may be provided in a fourth container of a plurality of fourth medical visualisation devices.

The packagings and/or containers may be provided with a colour marking corresponding to the colour marking of the respective device. For example, the first packaging may comprise a first packaging colour identifier, which may be of the first colour. The first container may comprise a first container colour identifier, which may be of the first colour. The second packaging may comprise a second packaging colour identifier, which may be of the second colour. The second container may comprise a second container colour identifier, which may be of the second colour. The third packaging may comprise a third packaging colour identifier, which may be of the third colour. The third container may comprise a third container colour identifier, which may be of the third colour. The fourth packaging may comprise a fourth packaging colour identifier, which may be of the fourth colour. The fourth container may comprise a fourth container colour identifier, which may be of the fourth colour.

By providing the packagings and/or containers with colour coding indicating the type of medical visualisation device, the likelihood of unpacking a wrong device for a given clinical procedure is reduced. Alternatively or additionally, the packaging(s) may be at least partly transparent to facilitate the same, e.g. to allow the operator to identify colour markings on the medical visualisation device inside the packaging.

The first medical visualisation device, the second medical visualisation device, the third medical visualisation device and/or the fourth medical visualisation device may be configured to generate a view from the distal end of the insertion tube, e.g. by the image sensor, which may be arranged at the distal tube end.

The first image sensor and the second image sensor may be a similar image sensor type, e.g. a primary image sensor type. The first image sensor may be the primary image sensor type. The second image sensor may be the primary image sensor type. The one or more connector ports may include a primary connector port. The primary connector port may be adapted to receive the first connector. The primary connector port may be adapted to receive the second connector. The primary connector port may be adapted to receive connectors of visualisation devices comprising an image sensor being the primary image sensor type.

The third image sensor may be a secondary image sensor type. The one or more connector ports may include a secondary connector port. The secondary connector port may be adapted to receive the third connector. The secondary connector port may be adapted to receive connectors of visualisation devices comprising an image sensor being the secondary image sensor type.

The fourth image sensor may be the primary image sensor type, the secondary image sensor type or a tertiary image sensor type.

The connectors may comprise connector colour identifiers indicative of the image sensor type of the respective medical visualisation device. The first connector may comprise a first connector colour identifier. The second connector may comprise a second connector colour identifier. The third connector may comprise a third connector colour identifier. The fourth connector may comprise a fourth connector colour identifier. The connector ports may comprise port colour identifiers indicative of the image sensor type which are compatible with the respective connector port. The primary connector port may comprise a primary port colour identifier. The secondary connector port may comprise a secondary port colour identifier. The first connector colour identifier, the second connector colour identifier and the primary port colour identifier may be a primary connector colour indicative of the primary image sensor type. The third connector colour identifier, optionally the fourth connector colour identifier and the secondary port colour identifier may be a secondary connector colour indicative of the secondary image sensor type.

The primary connector colour may have a primary connector hue angle. The secondary connector colour may have a secondary connector hue angle. The primary connector hue angle and the secondary connector hue angle may differ by more than 40 degrees. Thereby, the image sensor types may be colour-coded, to facilitate easy recognition of compatible connectors and connector ports.

The primary connector colour may have a primary connector chroma value. The primary connector chroma value may be more than 10, such as more than 20, such as more than 35, such as more than 50, such as more than 60, such as more than 70. The secondary connector colour may have a secondary connector chroma value. The secondary connector chroma value may be more than 10, such as more than 20, such as more than 35, such as more than 50, such as more than 60, such as more than 70.

The primary connector colour may have a primary connector lightness value. The primary connector lightness value may be more than 5, such as more than 10, such as more than 20, such as more than 30, such as more than 50. The secondary connector colour may have a secondary connector lightness value. The secondary connector lightness value may be more than 5, such as more than 10, such as more than 20, such as more than 30, such as more than 50.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Figure 1:
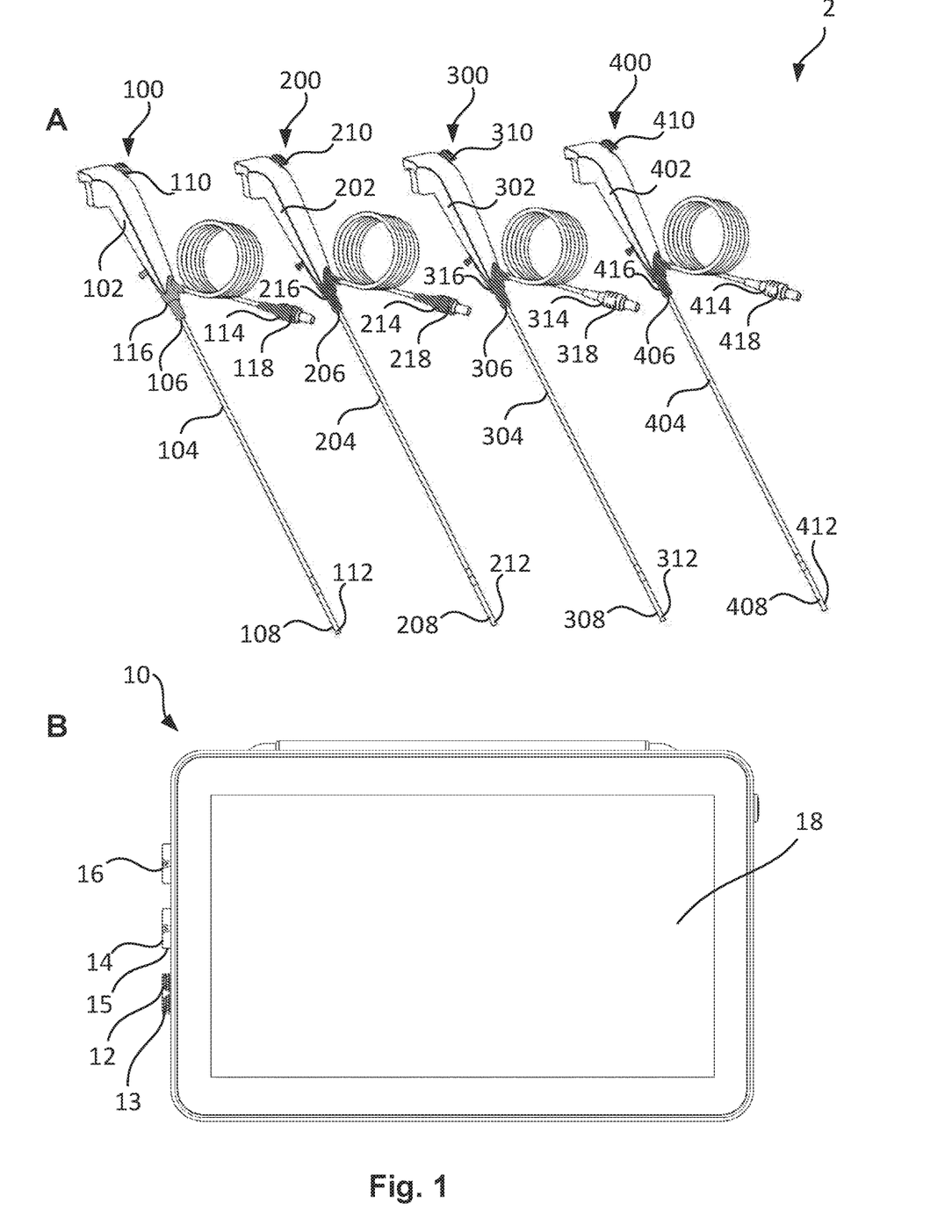
FIG. 1 is a schematic diagram illustrating an exemplary visualisation system.

FIG. 1 is a schematic diagram illustrating an exemplary visualisation system 2 comprising exemplary first medical visualisation device 100, second medical visualisation device 200, third medical visualisation device 300, and fourth medical visualisation device 400, illustrated in FIG. 1A, and an exemplary monitor device 10, illustrated in FIG. 1B.

Each of the visualisation devices 100, 200, 300, 400 comprises a handle 102, 202, 302, 304 and an insertion tube 104, 204, 304, 404. The insertion tube 104, 204, 304, 404 extends from the handle 102, 202, 302, 304, e.g. from a proximal tube end 106, 206, 306, 406, to a distal tube end 108, 208, 308, 408. The insertion tube 104, 204, 304, 404 may be at least partly flexible, and may comprise a bendable section, e.g. near the distal tube end 108, 208, 308, 408, which may be operated to direct the distal tube end 108, 208, 308, 408 in a desired direction. The medical visualisation devices 100, 200, 300, 400 may comprises control knobs 110, 210, 310, 410, which may be operated to direct the distal tube end 108, 208, 308, 408 in a desired direction.

Each of the visualisation devices 100, 200, 300, 400 may comprise an image sensor 112, 212, 312, 412, which may be arranged at the distal tube end 108, 208, 308, 408, as illustrated. In other embodiments, the image sensor 112, 212, 312, 412 may be arranged at a distance from the distal tube end 108, 208, 308, 408, and fibre optics may transmit the light received from the distal tube end 108, 208, 308, 408 to the image sensor 112, 212, 312, 412.

Each of the visualisation devices 100, 200, 300, 400 comprises a connector 114, 214, 314, 414 configured to be received by a connector port 12, 14, 16 of the monitor device 10, such as to allow display, on a display 18 of the monitor device 10, of an image representative of a view from the distal tube end 108, 208, 308, 408 of the visualisation device 100, 200, 300, 400, e.g. from the image sensor 112, 212, 312, 412. In some embodiments, the monitor device 10 may be configured to transmit an image signal to an external display (not shown), to allow display on the external display of the image representative of the view from the distal tube end 108, 208, 308, 408. In some embodiments, the monitor device 10 may be devoid of a display.

The medical visualisation devices 100, 200, 300, 400 may be configured for different types of clinical procedures. For example, the first medical visualisation device 100 may be a first device type configured for a first clinical purpose, e.g. urology. The second medical visualisation device 200 may be a second device type configured for a second clinical purpose, e.g. gastroenterology. The third medical visualisation device 300 may be a third device type configured for a third clinical purpose, e.g. pulmonology. The fourth medical visualisation device 400 may be a fourth device type configured for a fourth clinical purpose, e.g. rhinoscopy.

Each of the visualisation devices 100, 200, 300, 400 comprises a device colour identifier indicative of the clinical purpose of the visualisation device. The first medical visualisation device 100 comprises a first device colour identifier 116 being a first colour. The second medical visualisation device 200 comprises a second device colour identifier 216 being a second colour. The third medical visualisation device 300 comprises a third device colour identifier 316 being a third colour. The fourth medical visualisation device 400 comprises a fourth device colour identifier 416 being a fourth colour.

The device colour identifiers 116, 216, 316, 416 may comprise one or more coloured portions of the handle and/or of the insertion tube of the respective device. For example, the device colour identifier may include colouring of the control knob 110, 210, 310, 410 and/or of an interface between the handle 102, 202, 302, 304 and the insertion tube 104, 204, 304, 404, e.g. a transition portion of the handle 102, 202, 302, 304, which may enclose a proximal portion of the insertion tube 104, 204, 304, 404. The majority, such as the remainder, of the handle and/or the insertion tube may be a white, light greyish, dark greyish or black colour.

To distinguish the colours of the device colour identifiers 116, 216, 316, 416, and allow easy oral reference to them, the colours are chosen to differ by a minimum hue angle, e.g. as defined by the CIELCh colour space. Thus, a hue angle of each of the colours may differ by more than 40 degrees from hue angles of the other colours. Thereby, the colour of the device colour identifiers 116, 216, 316, 416, provides for easy identification of the device type, and reduces the likelihood of unpacking a wrong device for a given clinical procedure.

The image sensors 112, 212, 312, 412 of the medical visualisation devices 100, 200, 300, 400 may be different, but may also be the same for some of the devices, although their intended clinical procedures are different. For example, some of the image sensors 112, 212, 312, 412 may differ by image resolution. In an example, the first image sensor 112 and the second image sensor 212 is of a similar image sensor type, e.g. a primary image sensor type, and the third image sensor 312 and the fourth image sensor 412 is of another similar image sensor type, e.g. a secondary image sensor type.

The connector ports 12, 14, 16 of the monitor device 10 include a primary connector port 12 adapted to receive connectors of visualisation devices comprising image sensors of the primary image sensor type, i.e. the first connector 114 and the second connector 214. The connector ports 12, 14, 16 further includes a secondary connector port 14 adapted to receive connectors of visualisation devices comprising image sensors of the secondary image sensor type, i.e. the third connector 314 and the fourth connector 414. The connector ports 12, 14, 16 may, as illustrated, by provided on the side of the monitor device 10, e.g. protruding from the side of the monitor device 10.

To allow easy reference of the compatibility between connectors and connector ports, the connector and the connector ports may be provided with colour identifiers. For example, the first connector 114 may comprise a first connector colour identifier 118 being a primary connector colour indicative of the primary image sensor type. The second connector 214 may comprise a second connector colour identifier 218 being the primary connector colour, i.e. the same as the first connector colour identifier 118, indicative of the primary image sensor type. The third connector 314 may comprise a third connector colour identifier 318 being a secondary connector colour, e.g. different from the primary connector colour, indicative of the secondary image sensor type. The fourth connector 414 may comprise a fourth connector colour identifier 418 being the secondary connector colour indicative of the secondary image sensor type.

The primary connector port 12, adapted to receive connectors of visualisation devices comprising image sensors of the primary image sensor type, comprises a primary port colour identifier 13, being the primary connector colour. The secondary connector port 14, adapted to receive connectors of visualisation devices comprising image sensors of the secondary image sensor type, comprises a secondary port colour identifier 15, being the secondary connector colour.

By the provision of the connector ports 12, 14, 16, and particularly the port colour identifiers 13, 15, to protrude from the side of the monitor device, the connector ports 12, 14, 16 and/or the port colour identifiers 13, 15 may be easily localised and recognised from a front view of the monitor device 10.

To distinguish the colours of the connector colours, the colours may be chosen to differ by a minimum hue angle, e.g. as defined by the CIELCh colour space. Thus, a hue angle of each of the connector colours may differ by more than 40 degrees from hue angles of the other connector colours. Thereby, the connector colours, provides for easy identification of the image sensor technology and facilitates easy identification of compatible connectors and connector ports.

Figure 2:
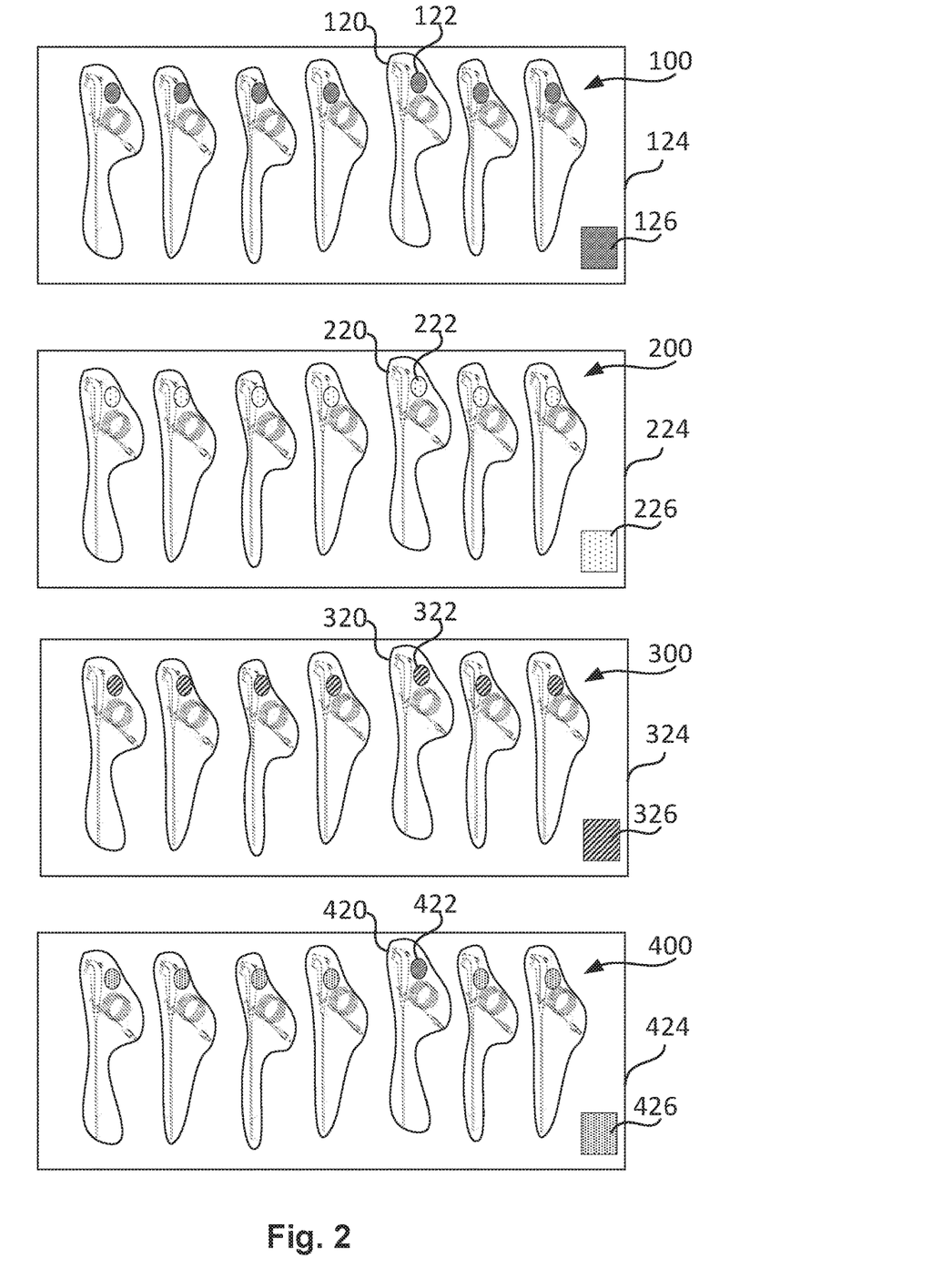
FIG. 2 is a schematic diagram illustrating a plurality of containers with medical visualisation devices.

FIG. 2 is a schematic diagram illustrating a plurality of containers 124, 224, 324, 424 with a plurality of packaged medical visualisation devices 100, 200, 300, 400. Each of the medical visualisation devices 100, 200, 300, 400 are individually packaged in a packaging 120, 220, 320, 420, which may be sealed to maintain sterility of the device.

The plurality of first medical visualisation devices 100 are packaged in first packagings 120. The plurality of second medical visualisation devices 200 are packaged in second packagings 220. The plurality of third medical visualisation devices 300 are packaged in third packagings 320. The plurality of fourth medical visualisation devices 400 are packaged in fourth packagings 420.

The medical visualisation devices 100, 200, 300, 400 are provided in containers 124, 224, 324, 424. The first medical visualisation devices 100 are provided in a first container 124. The second medical visualisation devices 200 are provided in a second container 224. The third medical visualisation devices 300 are provided in a third container 324. The fourth medical visualisation devices are provided in a fourth container 424.

The packagings 120, 220, 320, 420 and the containers 124, 224, 324, 424 are provided with colour identifiers corresponding to the colour identifier of the respective devices 100, 200, 300, 400. For example, the first packagings 120 comprise first packaging colour identifiers 122, which may be of the first colour, i.e. the same colour as described above for the first device colour identifier 116 (see FIG. 1). Furthermore, the first container 124 comprises a first container colour identifier 126, which may also be of the first colour. The second packagings 220 comprise second packaging colour identifiers 222, which may be of the second colour, i.e. the same colour as described above for the second device colour identifier 216 (see FIG. 1). Furthermore, the second container 224 comprises a second container colour identifier 226, which may also be of the first colour. The third packagings 320 comprise third packaging colour identifiers 322, which may be of the third colour, i.e. the same colour as described above for the third device colour identifier 316 (see FIG. 1). Furthermore, the third container 324 comprises a third container colour identifier 326, which may also be of the third colour. The fourth packagings 420 comprise fourth packaging colour identifiers 422, which may be of the fourth colour, i.e. the same colour as described above for the fourth device colour identifier 416 (see FIG. 1). Furthermore, the fourth container 424 comprises a fourth container colour identifier 426, which may also be of the fourth colour.

The disclosure has been described with reference to a preferred embodiment. However, the scope of the invention is not limited to the illustrated embodiment, and alterations and modifications can be carried out without deviating from the scope of the invention.

Throughout the description, the use of the terms "first", "second", "third", "fourth", "primary", "secondary", "tertiary" etc. does not imply any particular order or importance but are included to identify individual elements. Furthermore, the labelling of a first element does not imply the presence of a second element and vice versa.

LIST OF REFERENCES

2 Medical visualisation system
10 monitor device
12 primary connector port
14 secondary connector port
16 tertiary connector port
18 display
100 first medical visualisation device
102 first handle
104 first insertion tube
106 first proximal tube end
108 first distal tube end 110 first control knob
112 first image sensor
114 first connector
116 first device colour identifier
118 first connector colour identifier
120 first packaging
122 first packaging colour identifier
124 first container
126 first container colour identifier
200 second medical visualisation device
202 second handle
204 second insertion tube
206 second proximal tube end
208 second distal tube end
210 second control knob
212 second image sensor
214 second connector
216 second device colour identifier
218 second connector colour identifier
220 second packaging
222 second packaging colour identifier
224 second container
226 second container colour identifier
300 third medical visualisation device
302 third handle
304 third insertion tube
306 third proximal tube end
308 third distal tube end
310 third control knob
312 third image sensor
314 third connector
316 third device colour identifier
318 third connector colour identifier
320 third packaging
322 third packaging colour identifier
324 third container
326 third container colour identifier
400 fourth medical visualisation device
402 fourth handle
404 fourth insertion tube
406 fourth proximal tube end
408 fourth distal tube end
410 fourth control knob
412 fourth image sensor
414 fourth connector
416 fourth device colour identifier
418 fourth connector colour identifier
420 fourth packaging
422 fourth packaging colour identifier
424 fourth container
426 fourth container colour identifier

We claim:

1. A medical visualisation system comprising:
a first medical visualisation device of a first device type configured for a first clinical purpose and including a first image sensor, a first connector, and a first device color identifier corresponding to the first device type, the first device color identifier comprising a first color having a first hue angle;
a second medical visualisation device of a second device type configured for a second clinical purpose and including a second image sensor, a second connector, and a second device color identifier corresponding to the second device type, the second device color identifier comprising a second color having a second hue angle;
a third medical visualisation device of a third device type configured for a third clinical purpose and including a third image sensor, a third connector, and a third device color identifier corresponding to the third device type, the third device color identifier comprising a third color having a third hue angle; and
a monitor device comprising one or more connector ports adapted to receive one or more of the first connector, the second connector, and the third connector,
wherein the first hue angle and the second hue angle differ by more than 40 degrees, the second hue angle and the third hue angle differ by more than 40 degrees, and the third hue angle and the first hue angle differ by more than 40 degrees, and
wherein the first image sensor is a primary image sensor type, and the second image sensor is the primary image sensor type, and wherein the one or more connector ports includes a primary connector port adapted to receive the first connector and the second connector, the first connector comprising a first connector color identifier and the second connector comprising a second connector color identifier, the primary connector port comprising a primary port color identifier, the first connector color identifier, the second connector color identifier and the primary port color identifier being a primary connector color indicative of the primary image sensor type.

2. The medical visualisation system of claim 1, wherein the first hue angle and the second hue angle differ by more than 80 degrees.

3. The medical visualisation system of claim 1, wherein the first device type is a urology endoscope, the second device type is a gastro-intestinal endoscope, and the third device type is a pulmonology endoscope.

4. The medical visualisation system of claim 1, wherein the first hue angle is between 90-120 degrees, the second hue angle is between 250-280 degrees, and/or the third hue angle is between 5-35 degrees.

5. The medical visualisation system according to claim 1, further comprising a fourth medical visualisation device of a fourth device type configured for a fourth clinical purpose and including a fourth image sensor, a fourth connector, and a fourth device color identifier corresponding to the fourth device type, the fourth device color identifier comprising a fourth color having a fourth hue angle, and the fourth hue angle differing by more than 40 degrees from the first hue angle, the second hue angle, and the third hue angle.

6. The medical visualisation system of claim 5, wherein the fourth device type is a rhino-laryngo endoscope.

7. The medical visualisation system of claim 5, wherein the first color has a first chroma value, the second color has a second chroma value, the third color has a third chroma value, and/or the fourth color has a fourth chroma value, and wherein the first chroma value, the second chroma value, the third chroma value and/or the fourth chroma value, in a range of 0-100, are more than 10.

8. The medical visualisation system of claim 5, wherein the first color has a first lightness value, the second color has a second lightness value, the third color has a third lightness value, and/or the fourth color has a fourth lightness value, and wherein the first lightness value, the second lightness value, the third lightness value and/or the fourth lightness value, in a range of 0-100, are more than 5, and wherein the first lightness value, the second lightness value, the third lightness value and/or the fourth lightness value, are less than 90.

9. The medical visualisation system of claim 8, wherein the first color has a first chroma value, the second color has a second chroma value, the third color has a third chroma value, and/or the fourth color has a fourth chroma value, wherein the first chroma value, the second chroma value, the third chroma value and/or the fourth chroma value, in a range of 0-100, are more than 10, wherein the first hue angle, the second hue angle, the third hue angle and/or the fourth hue angle are hue angles of the CIELCh color space and/or the first chroma value, the second chroma value, the third chroma value and/or the fourth chroma value are chroma values of the CIELCh color space and/or the first lightness value, the second lightness value, the third lightness value and/or the fourth lightness value are lightness values of the CIELCh color space.

10. The medical visualisation system of claim 5, wherein the first medical visualisation device, the second medical visualisation device, the third medical visualisation device and/or the fourth medical visualisation device comprises a handle and an insertion tube extending from the handle to a distal tube end, and being configured to generate a view from the distal tube end of the insertion tube.

11. The medical visualisation system of claim 1, wherein the third image sensor is a secondary image sensor type, and wherein the one or more connector ports includes a secondary connector port adapted to receive the third connector, the third connector comprising a third connector color identifier and the secondary connector port comprising a secondary port color identifier, the third connector color identifier and the secondary port color identifier being a secondary connector color.

12. The medical visualisation system of claim 11, wherein the primary connector color has a primary connector hue angle, the secondary connector color has a secondary connector hue angle, and wherein the primary connector hue angle and the secondary connector hue angle differ by more than 40 degrees.

13. The medical visualisation system of claim 1, wherein each of the first medical visualisation device, the second medical visualisation device, and the third medical visualisation device comprises a handle, an insertion tube extending from the handle to a distal tube end, and at the distal tube end, one of, respectivelly, the first image sensor, the second image sensor, and the third image sensor.

14. The medical visualisation system of claim 13, wherein the first hue angle is between 90-120 degrees, the second hue angle is between 250-280 degrees, and the third hue angle is between 5-35 degrees.

15. The medical visualisation system of claim 13, wherein the first color has a first lightness value, the second color has a second lightness value, and the third color has a third lightness value, and wherein the first lightness value, the second lightness value, and the third lightness value, in a range of 0-100, are more than 5.

16. The medical visualisation system of claim 15, wherein the first color has a first chroma value, the second color has a second chroma value, and the third color has a third chroma value, wherein the first chroma value, the second chroma value, and the third chroma value, in a range of 0-100, are more than 10.

17. The medical visualisation system of claim 16, wherein the first hue angle, the second hue angle, and the third hue angle are hue angles of the CIELCh color space and/or the first chroma value, the second chroma value, and the third chroma value are chroma values of the CIELCh color space and/or the first lightness value, the second lightness value, and the third lightness value are lightness values of the CIELCh color space.

18. The medical visualisation system of claim 17, wherein the lightness values are in a range between 10 and 100.

19. The medical visualisation system of claim 1, further comprising a first packaging, a second packaging, and a third packaging, wherein the first medical visualisation device is packaged in the first packaging, the second medical visualisation device is packaged in the second packaging, and the third medical visualisation device is packaged in the third packaging.

20. The medical visualisation system of claim 19, wherein the first packaging, the second packaging, and the third packaging, are transparent.

21. The medical visualisation system of claim 19, wherein the first packaging includes a first packaging colour identifier comprising the first color, the second packaging includes a second packaging colour identifier comprising the second color, and the third packaging includes a third packaging colour identifier comprising the third color.

* * * * *